United States Patent [19]

Boden et al.

[11] Patent Number: 4,594,464
[45] Date of Patent: Jun. 10, 1986

[54] METHYL PHENETHYL ACETAL OF 2-BUTYNAL

[75] Inventors: Richard M. Boden, Ocean; Joseph A. McGhie, South Orange, both of N.J.

[73] Assignee: International Flavors & Fragrances Inc., New York, N.Y.

[21] Appl. No.: 742,273

[22] Filed: Jun. 7, 1985

Related U.S. Application Data

[62] Division of Ser. No. 609,345, May 11, 1984.

[51] Int. Cl.[4] ............................................. C07C 43/164
[52] U.S. Cl. ................................. 568/592; 252/522 R
[58] Field of Search ......................................... 568/592

[56] References Cited

U.S. PATENT DOCUMENTS 2,000,252  5/1935  Reppe et al. ................. 568/592
3,632,860  1/1972  Marbet ...................... 568/592 X

OTHER PUBLICATIONS

Shostakovskii et al, Chem. Abs., vol. 54, No. 9 (1960) 8598–8599.

Primary Examiner—Bernard Helfin
Attorney, Agent, or Firm—Arthur L. Liberman

[57] ABSTRACT

Described is the compound having the structure:

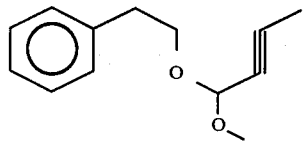

as well as mixtures thereof with the compounds having the structures:

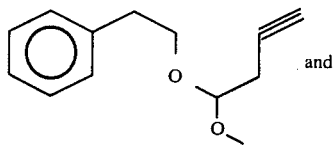

and

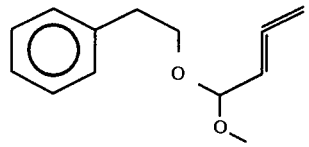

and a method for preparing same involving the reaction of the compound having the structure:

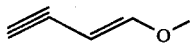

with beta-phenylethyl alcohol having the structure:

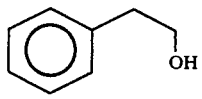

as well as uses thereof in augmenting or enhancing the aroma of perfume compositions, colognes and perfumed articles including solid or liquid anionic, cationic, nonionic or zwitterionic detergents, fabric softener compositions, fabric softener articles, cosmetic powders, hair preparations and perfumed polymers.

5 Claims, 5 Drawing Figures

GLC PROFILE FOR EXAMPLE I.
CRUDE

IR SPECTRUM FOR FRACTION 5 OF EXAMPLE I, GLC PEAK 10.

GLC PROFILE FOR FRACTION 3 OF EXAMPLE II.
FIRST DISTILLATION

GLC PROFILE FOR EXAMPLE II.
CRUDE

METHYL PHENETHYL ACETAL OF 2-BUTYNAL

This is a divisional of application Ser. No. 609,345, filed 5/11/84.

BACKGROUND OF THE INVENTION

Materials which can provide sweet, floral, hyacinth-like, fruity, pineapple and apple aromas with peony, hyacinth and green topnotes, particularly those materials having such organoleptic properties which are relatively inexpensive are highly sought after in the art of perfumery. Many of the natural materials which provide such fragrance profiles and which contribute desired nuances to perfumery compositions and perfumed articles are high in cost, vary in quality from one batch to another and/or are generally subject to the usual variations of natural products.

There is, accordingly, a continuing effort to find synthetic materials which will replace the essential fragrance notes produced by natural essential oils or compositions thereof. Unfortunately, many of these synthetic materials either have the desired nuances only to a relatively small degree or else contribute undesirable or unwanted odor to the composition. The search for materials which can provide a more refined hyacinth aroma having hyacinth topnotes has been difficult and relatively costly in the areas of both natural products and synthetic products.

No chemicals in the prior art have a structure similar to the chemicals produced by our invention and no such chemicals have an organoleptic profile even somewhat similar to that of the composition of matter of our invention.

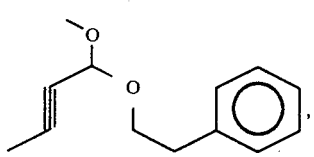

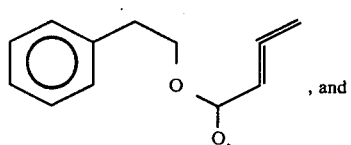

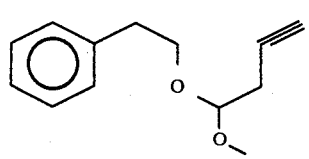

Figure 1:
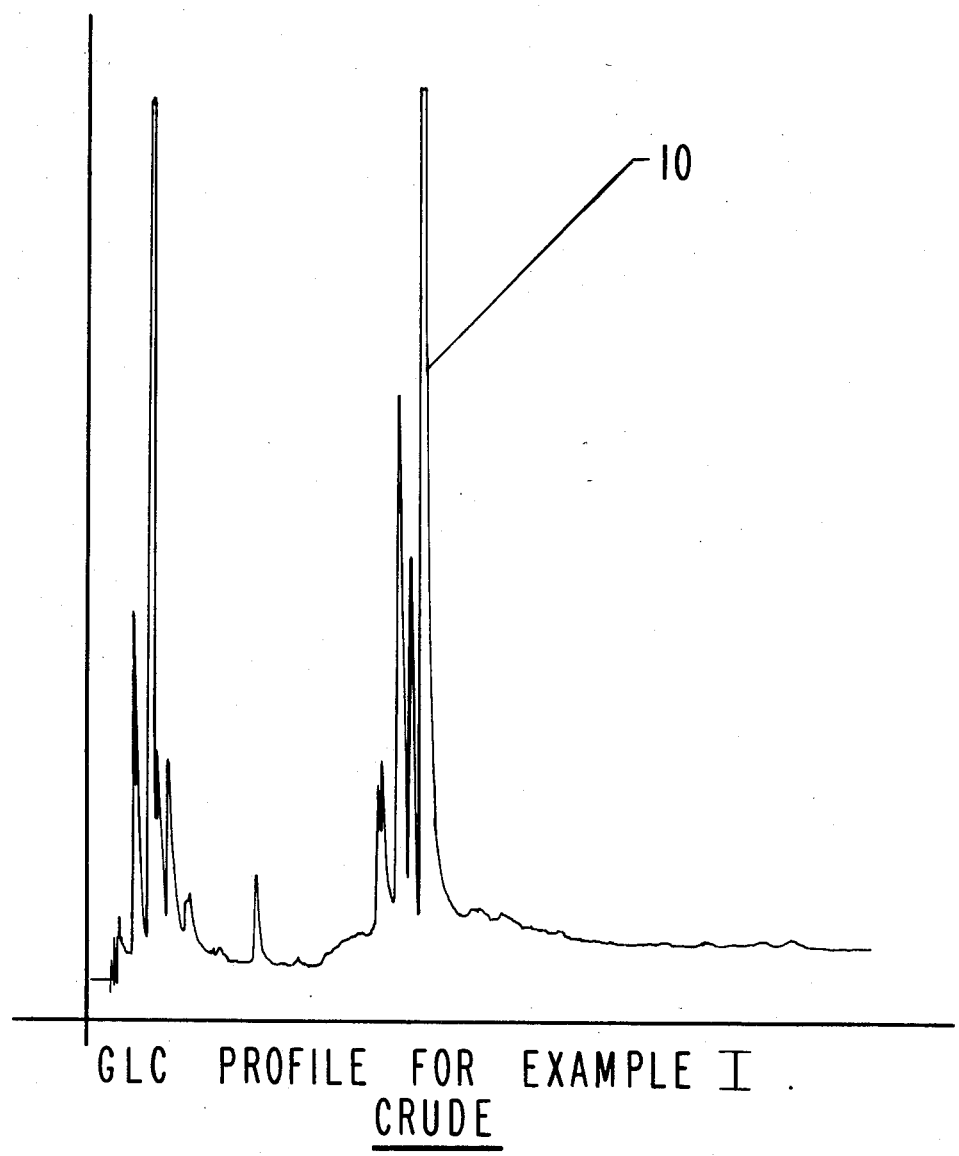
FIG. 1 is the GLC profile for the crude reaction product of Example I containing the compounds having the structures.
Figure 2:
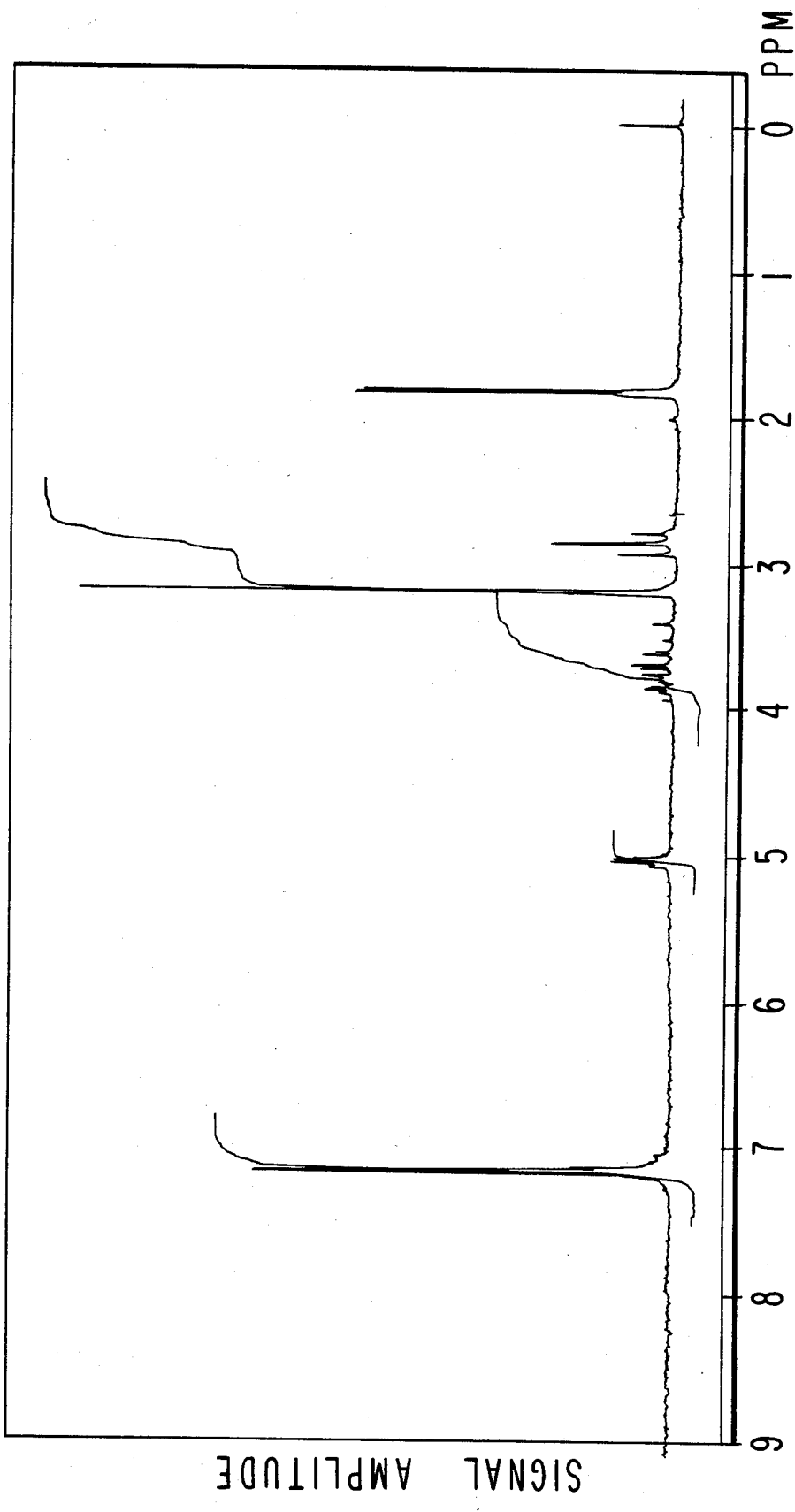

FIG. 2 is the NMR spectrum for the GLC peak indicated as peak "10" in FIG. 1, of fraction 5 of the distillation of the reaction product of Example I for the compound having the structure:

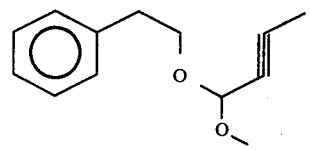

(Conditions: Field strength: 100 MHz; solvent: CFCl₃).

Figure 3:
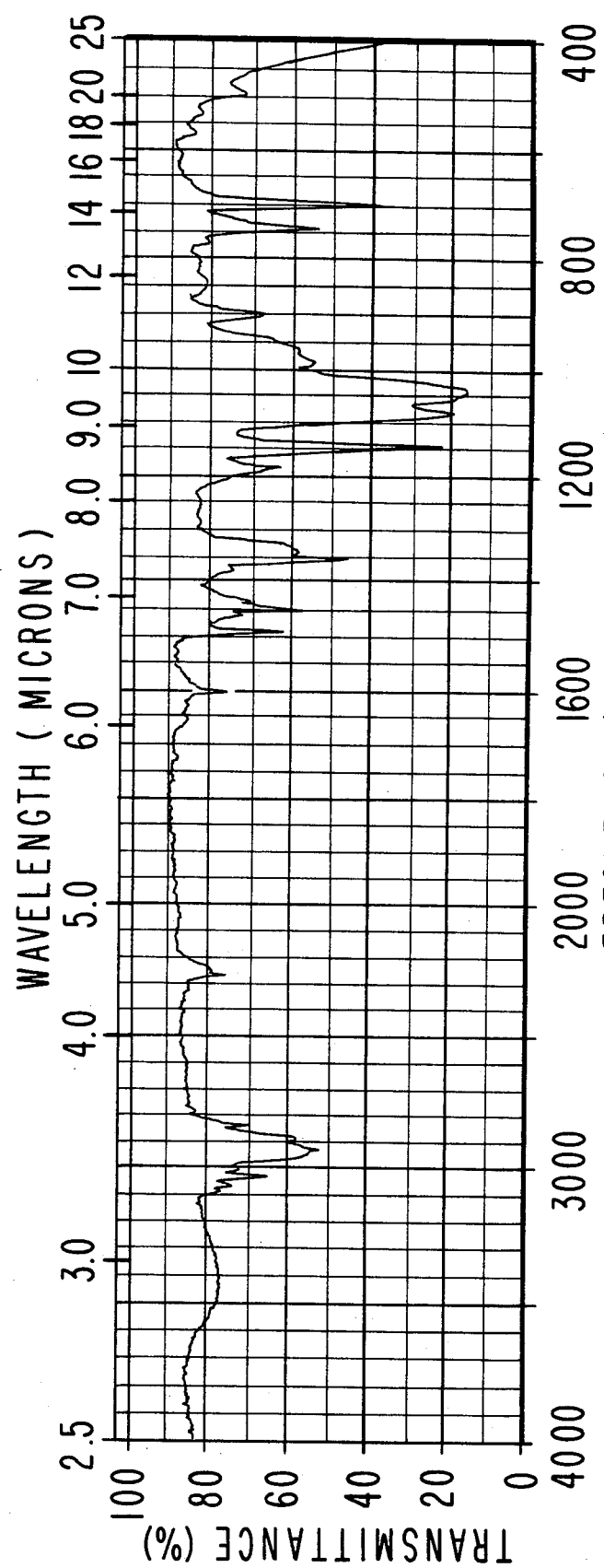

FIG. 3 is the infra-red spectrum for the GLC peak of FIG. 1 indicated by reference numeral "10", of fraction 5 of the distillation of the reaction product of Example I for the compound having the structure:

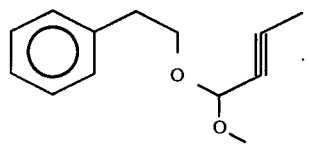

Figure 4:
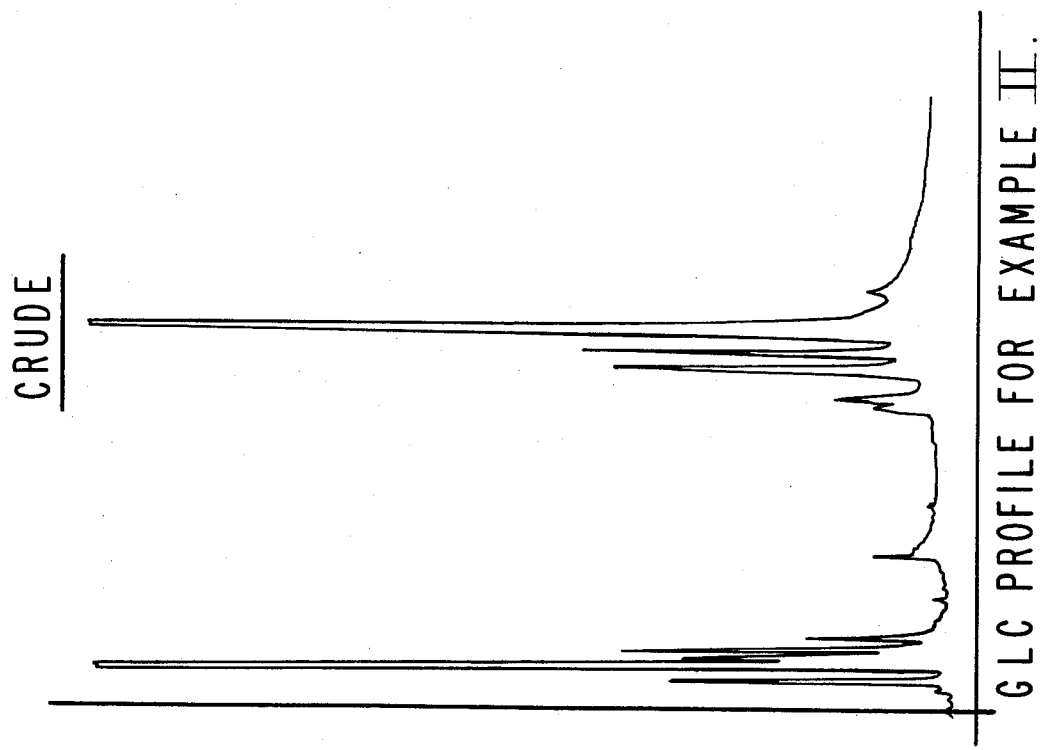

FIG. 4 is the GLC profile for the crude reaction product of Example II containing the compounds having the structures:

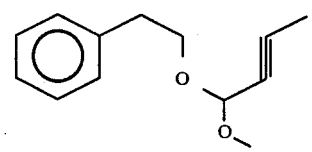

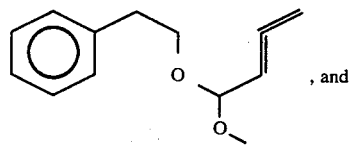

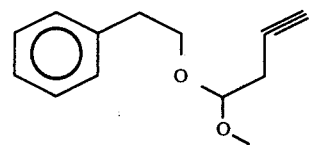

Figure 5:
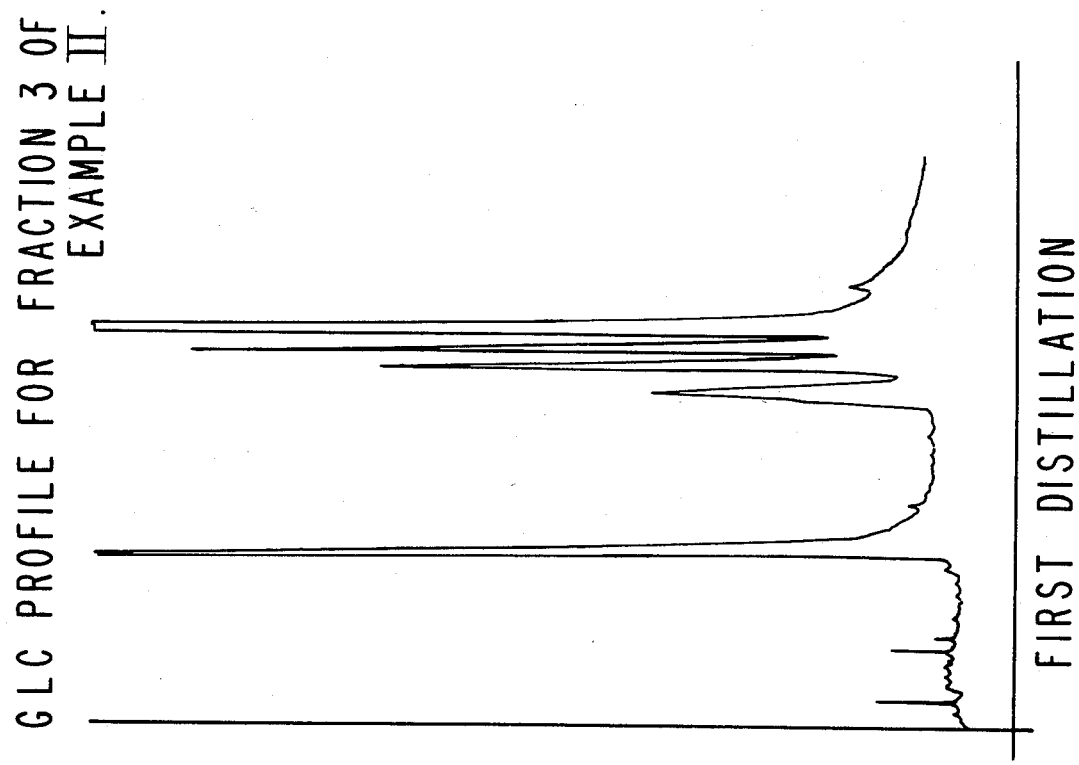

FIG. 5 is the GLC profile for fraction 3 of the first distillation of the reaction product of Example II containing the compounds having the structures:

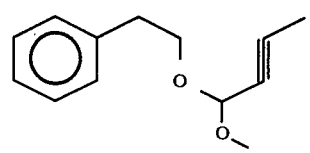

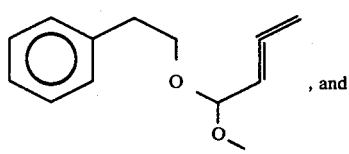

-continued

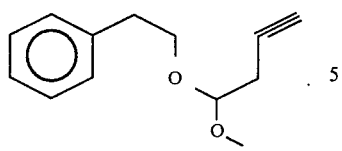

DETAILED DESCRIPTION OF THE DRAWINGS

The peak indicated by Reference Numeral 10 in FIG. 1 is the peak for the compound having the structure:

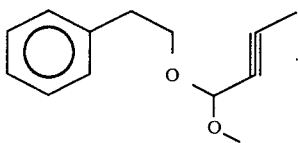

THE INVENTION

It has now been determined that a certain acetal defined according to the structure:

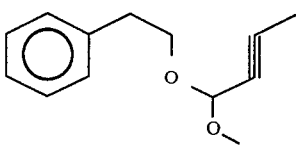

and mixtures thereof with compounds having the structures:

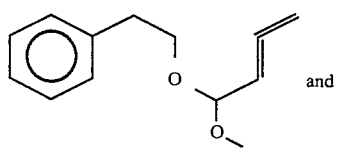

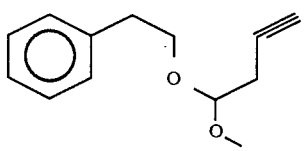

are capable of imparting a variety of fragrances to various consumable materials.

Briefly, our invention contemplates the compounds defined according to structures:

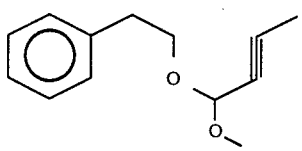

-continued

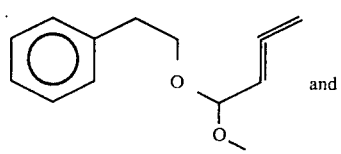

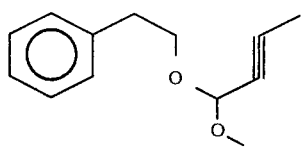

more specifically, the compound having the structure:

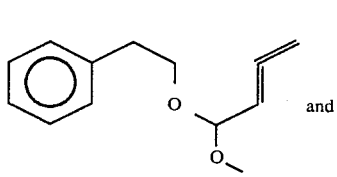

taken alone or taken in admixture with the compounds having the structures:

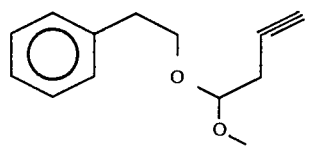

The acetals of our invention may be prepared by reacting beta-phenylethyl alcohol defined according to the structure:

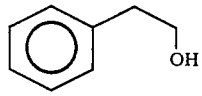

with the compound having the structure:

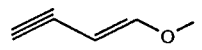

according to the reaction:

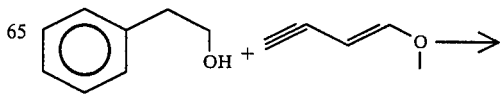

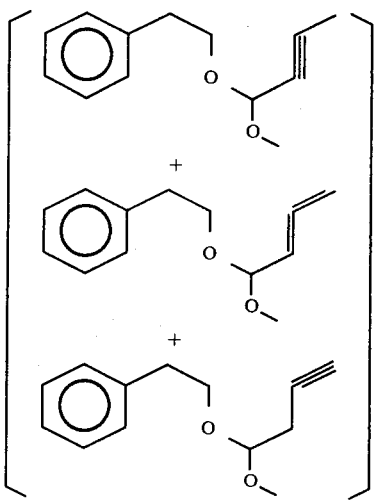

In this reaction, the mole ratio of compound having the structure:

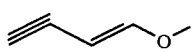

to beta-phenylethyl alcohol is about 1:1. If any material is used in slight excess, it is the compound having the structure:

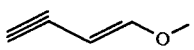

The reaction takes place at 100°–150° C. at about atmospheric pressure. The time of reaction is between about 2 and about 15 hours.

The reaction takes place in a solvent which is inert to the reactants and the reaction products, preferably toluene or a mixture of toluene and a methyl alcohol.

The reaction takes place in a presence of a catalyst, preferably sodium hydride or potassium hydride.

The mole ratio of hydride catalyst to beta-phenylethyl alcohol may vary from about 0.01:1 up to about 0.05:1.

The concentration of beta-phenylethyl alcohol reactant in the reaction mass may vary from about 2 up about 6 moles per liter.

At the end of the reaction, the reaction mass is washed with water and the solvent is stripped from the organic phase. The organic phase is then distilled yielding the compounds defined according to the structures:

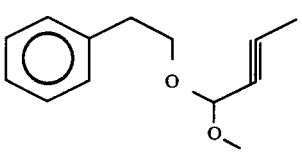

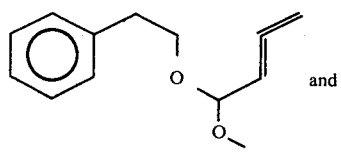

with a predominant amount of the compound having the structure:

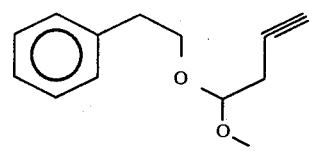

being present. In a typical reaction, the reaction product contains 75% of the compound having the structure:

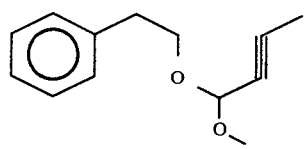

and 25% of the compound having the structure:

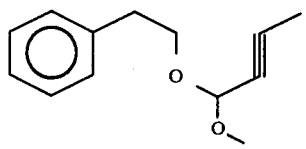

with trace amounts of the compound having the structure:

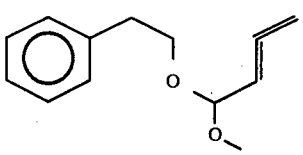

being present (Conditions: 10 hours at 105° C. using a sodium hydride catalyst and a toluene solvent).

The reaction mass is then fractionally distilled and fractions having desirable aroma nuances are collected for subsequent utilization for their organoleptic properties in augmenting or enhancing the aroma of colognes, perfumes and perfumed articles.

The acetals of our invention can be used to contribute sweet, floral, hyacinth, fruity, pineapple and apple aromas with peony, hyacinth and green topnotes. As olfactory agents, the acetals of our invention can be formulated into or used as components of a "perfume composition".

The term "perfume composition" is used herein to mean a mixture of organic compounds including, for example, alcohols, aldehydes, ketones, nitriles, esters, acetals other than the acetals of our invention and frequently hydrocarbons which are admixed so that the combined odors of the individual components produce a pleasant or desired fragrance. Such perfume compositions usually contain:

(a) the main note or the "bouquet" or foundation stone of the composition;
(b) modifiers which round off and accompany the main note;
(c) fixatives which include odorous substances which lend a particular note to the perfume throughout all stages of evaporation and substances which retard evaporation; and
(d) topnotes which are usually low boiling fresh smelling materials.

In perfume compositions, the individual component will contribute its particular olfactory characteristics but the overall effect of the perfume composition will be the sum of the effect of each of the ingredients. Thus, the individual compounds of this invention or mixtures thereof, can be used to alter the aroma characteristics of a perfume composition, for example, by highlighting or moderating the olfactory reaction contributed by another ingredient in the composition.

The amount of the acetals of our invention which will be effective in perfume compositions depends on many factors, including the other ingredients, their amounts, and the effects which are desired. It has been found that perfume compositions containing as little as 0.05% and as much as 15% of the acetals of our invention can be used to impart, augment or enhance sweet, floral, hyacinth, fruity, pineapple and apple aromas with peony, hyacinth and green topnotes to soaps, cosmetics, solid or liquid anionic, cationic, nonionic and zwitterionic detergents, perfumed polymers and other products. The amount employed can range up to 50% of the fragrance and can be as low as 0.05% of the fragrance and will depend on considerations of cost, nature of the end product, the effect desired on the finished product and the particular fragrance sought.

The acetals of our invention can be used alone or in a perfume composition as an olfactory component in detergents and soaps, space odorants and deodorants, perfumes, colognes, toilet waters, bath salts, hair preparations such as lacquers, brilliantines, pomades and shampoos, cosmetic preparations such as creams, deodorants, hand lotions and sun screens, powders such as talcs, dusting powders, face powders and the like.

When used as an olfactory component of a perfumed article as little as 0.01% of one or more of the acetals of our invention will suffice to impart a warm hyacinth aroma with sweet, floral, fruity, pineapple, apple and peony aroma nuances. Generally, no more than 5.0% is required. Thus, the range of use of the acetals of our invention in perfumed articles is from about 0.01% up about 5.0%.

In addition, the perfume compositions of our invention can contain a vehicle or carrier for the acetals taken alone or taken together with other ingredients. The vehicle can be a liquid such as an alcohol such as ethanol, glycol such as propylene glycol or the like. The carrier can also be an absorbent solid such as gum e.g., guar gum or xanthan gum or components for encapsulating the composition, e.g., gelatin when using coacervation.

The following Examples I and II are given to illustrate techniques for producing the compounds of our invention. Examples III and onwards are given to illustrate embodiments of our invention as it is presently preferred to practice it for utilizing the acetals of our invention. It will be understood that these examples are illustrative and the invention is not to be considered as restricted thereto except as indicated in the appended claims.

EXAMPLE I

Preparation of Methyl Phenethyl Diacetal of 2-Butynal

Reaction:

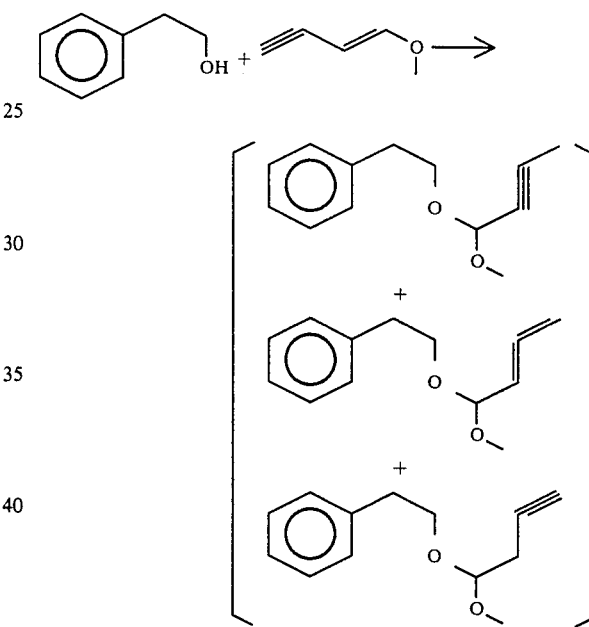

Into a 2 liter reaction vessel equipped with stirrer, thermometer, reflux condenser and addition funnel is placed 150 cc of anhydrous toluene and 282.0 grams of phenylethyl alcohol (2.3 moles) as well as 190.0 (2.317 moles) of 1-methoxy-1-buten-3-yne.

Over a period of 20 minutes, 3.0 grams (0.079 moles) of 50% sodium hydride is added to the reaction mass with stirring. The reaction mass is then heated to 105° C. with stirring and refluxing and maintained at reflux for a period of 10 hours.

At the end of the 10 hour period, the reaction mass is cooled to room temperature and 200 cc of water is added. The organic phase is separated from the aqueous phase. The organic phase is washed with one 250 cc volume of water and stripped of solvent.

The residue is distilled on a 12" stone packed column yielding the following fractions:

| FRACTION NO. | VAPOR TEMP. (°C.) | LIQUID TEMP. (°C.) | VACUUM mm/Hg. PRESSURE |
|---|---|---|---|
| 1 | 85/90 | 125/130 | 3.5/3.8 |

-continued

| FRACTION NO. | VAPOR TEMP. (°C.) | LIQUID TEMP. (°C.) | VACUUM mm/Hg. PRESSURE |
| --- | --- | --- | --- |
| 2 | 110 | 140 | 3.8 |
| 3 | 128 | 145 | 3.5 |
| 4 | 136 | 149 | 3.8 |
| 5 | 118 | 205 | 3.8 |
| 6 | 78 | 225 | 3.8 |

Fractions 3 and 4 are bulked. Bulked fractions 3 and 4 have a sweet, floral, hyacinth, fruity, pineapple and apple aroma with peony, hyacinth and green topnotes.

FIG. 1 is the GLC profile of the crude reaction product. The peak indicated by Reference Numeral 10 on this GLC profile is the peak for the compound having the structure:

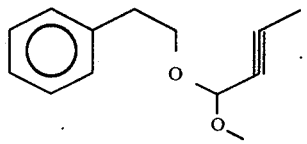

The other peaks are for the compounds having the structures:

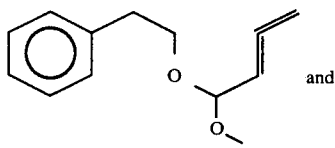

and

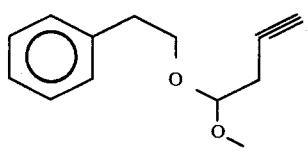

FIG. 2 is the NMR spectrum for the peak indicated by Reference Numeral 10 from the GLC profile of the crude reaction product. The same GLC profile is for fraction 5 of the foregoing distillation. It is for the compound having the structure:

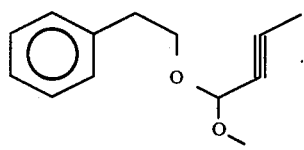

(Conditions: Field strength: 100 MHz; solvent: CFCl₃).

FIG. 3 is the infra-red spectrum for fraction 5 of the foregoing distillation containing the compound having the structure:

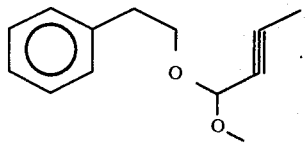

EXAMPLE II

Preparation of Methyl Phenethyl Diacetal of 2-Butynal

Reaction:

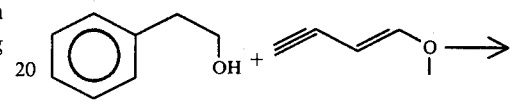

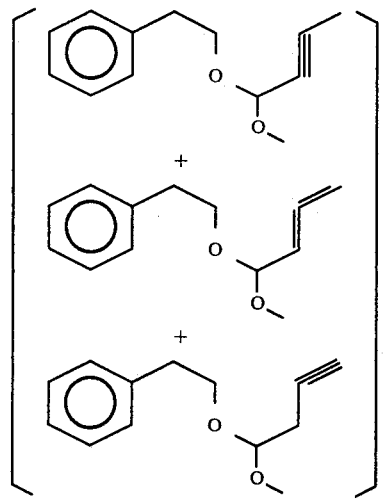

Into a 2 liter reaction flask equipped with stirrer, thermometer, reflux condenser and heating mantle is placed 150 cc of the 4:1 mixture of toluene and methanol. Over a period of 15 minutes, 3.8 grams of 50% sodium hydride is added to the solvent.

Over a period of 30 minutes, 282.0 grams (2.3 moles) of phenylethyl alcohol is slowly added to the reaction mass while maintaining the temperature of the reaction mass at 30° C.

Over a period of 10 minutes, 190.0 grams (2.3 moles) of 1-methoxy-1-buten-3-yne is added to the reaction mass while maintaining the reaction mass at 40° C. The reaction mass is then stirred at 40° C. for 15 minutes. The reaction mass is then heated to reflux and maintained at reflux conditions (120°–125° C.) for a period of 3 hours. At the end of the 3 hour period, the reaction mass is cooled to room temperature and washed as follows:

(i) two 300 cc portions of water; and
(ii) one 300 cc portion of saturated sodium chloride.

The toluene and methanol solvent are stripped off and the reaction mass is distilled on a 12″ packed column yielding the following fractions:

| FRACTION NO. | VAPOR TEMP. (°C.) | LIQUID TEMP. (°C.) | VACUUM mm/Hg. PRESSURE |
|---|---|---|---|
| 1 | 70/80 | 110/110 | 1.8/1.8 |
| 2 | 90 | 115 | 1.8 |
| 3 | 100 | 125 | 1.8 |
| 4 | 110 | 130 | 1.8 |
| 5 | 120 | 130 | 1.8 |
| 6 | 120 | 155 | 1.8 |
| 7 | 130 | 210 | 1.8 |

Fractions 3–7 are bulked and redistilled on a spinning bend column yielding the following fractions:

| FRACTION NO. | VAPOR TEMP. (°C.) | LIQUID TEMP. (°C.) | VACUUM mm/Hg. PRESSURE |
|---|---|---|---|
| 1 | 60/64 | 130/135 | .85/2.0 |
| 2 | 64 | 137 | 2.2 |
| 3 | 48 | 145 | 2.4 |
| 4 | 78 | 148 | 2.4 |
| 5 | 84 | 151 | 2.4 |
| 6 | 90 | 150 | 2.2 |
| 7 | 90 | 150 | 2.2 |
| 8 | 96 | 153 | 2.2 |
| 9 | 102 | 158 | 2.2 |
| 10 | 107 | 160 | 2.2 |
| 11 | 107 | 165 | 2.2 |
| 12 | 100 | 195 | 2.2 |
| 13 | 100 | 220 | 2.5 |

The resulting product has a sweet, floral, hyacinth, fruity, pineapple and apple aroma profile with peony, hyacinth and green topnotes.

The isomer defined according to the structure:

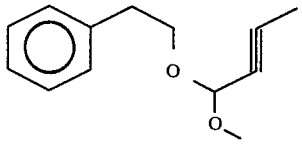

has an intense long-lasting fresh hyacinth aroma.

FIG. 4 is the GLC profile for the crude reaction product prior to distillation.

FIG. 5 is the GLC profile for fraction 3 of the first of the foregoing 2 distillations.

EXAMPLE III

Perfume Formulation

The following perfume formulation is prepared:

| INGREDIENTS | PARTS BY WEIGHT |
|---|---|
| Bergamot oil | 30 |
| Orris oil | 50 |
| Opoponax resinoid | 50 |
| Lemon oil | 20 |
| Jasmin natural | 70 |
| Bulgarian rose oil | 95 |
| Ginger oil | 80 |
| Galbanum resin | 80 |
| Vetiver oil | 95 |
| Violet essence | 50 |
| Costus oil | 80 |
| Neorli oil | 85 |
| Musk ambrette | 92 |
| Civetone | 81 |
| Red thyme oil | 21 |
| Methyl jasmonate | 18 |
| Castorium resinoid | 12 |
| Trans, trans delta-damascone | 52 |
| Mixture of compounds having the structures: 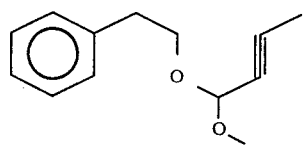 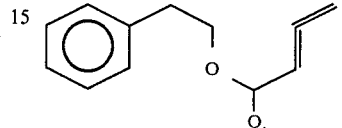 and 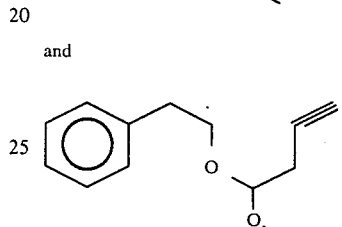 produced according to Example I (bulked distillation fractions 3 and 4) or produced according to Example II (second distillation: bulked fractions 5–8) | 17 |

The foregoing perfume formulation has an excellent opoponax and floral aroma with strong long lasting hyacinth notes and sweet, floral, fruity, pineapple, apple undertones with peony-like, hyacinth-like and green topnotes.

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| SUBSTANCE | AROMA DESCRIPTION |
|---|---|
| Mixture of compounds having the structures: | A sweet, floral, hyacinth, fruity, pineapple and apple aroma profile with peony-like, hyacinth and green topnotes. | and

TABLE I-continued

| SUBSTANCE | AROMA DESCRIPTION |
| --- | --- |
| produced according to Example I, bulked distillation fractions 3 and 4 or Example II, bulked second distillation fractions 5–8. Compound having the structure: 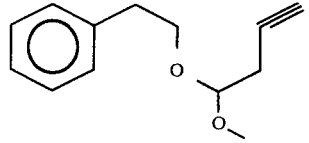 in pure form. | An intense long lasting natural fresh hyacinth aroma with green topnotes. |
| Perfume composition of Example III. | An opoponax and floral aroma with strong long lasting hyacinth notes and sweet, floral, fruity, pineapple, apple undertones with peony-like, hyacinth-like and green topnotes |

EXAMPLE V

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handerchief perfumes at all levels indicated.

EXAMPLE VII

Preparation of Soap Compositions

One hundred grams of soap chips [per sample] (IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

Preparation of Solid Detergent Compositions

Detergents are prepared using the following ingredients according to Example I of Canadian Pat. No. 1,007,948 (incorporated herein):

| INGREDIENT | PERCENT BY WEIGHT |
| --- | --- |
| "Neodol ® 45-11" (a $C_{14}C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener nonwoven fabrics and these aroma characteristics are described in Table I of Example IV, supra.

EXAMPLE X

The following hair spray formulation is prepared by first dissolving PBP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| INGREDIENT | PERCENT BY WEIGHT |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in TABLE I of Example IV | 0.10 |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 weight ratio of A:B and cooled to 45° C. and 0.3 weight percent of perfuming substance set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

A fabric conditioner produced according to the method of U.S. Pat. No. 4,291,072 issued on Sept. 22, 1981 is produced whereby the sheet consisting of nonwoven rayon substrate as set forth at column 3, lines 25-34 passed through the bath of molten cationic fabric softener-isopropenyl mixture is passed through the bath at 10 atmospheres pressure, during which time a fragrance material as set forth in Table I of Example IV is added at the rate of 0.35%. The resulting sheet when used with a clothing batch gives rise to a pleasant aroma in the head space above the clothing batch as set forth in Table I of Example IV.

What is claimed is:

1. An acetal selected from the group consisting of compounds having the structures:

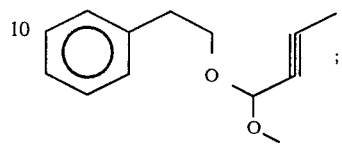

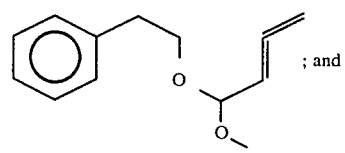

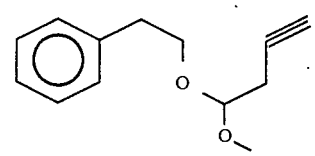

2. The compound of claim 1 having the structure:

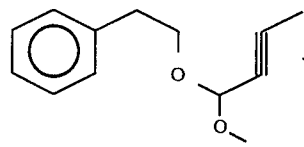

3. The product produced according to the process comprising the step of intimately admixing the compound having the structure:

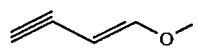

with beta-phenethyl alcohol having the structure:

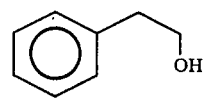

wherein the mole ratio of compound having the structure:

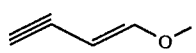

to beta-phenethyl alcohol is about 1:1 at a temperature in the range of from about 100° up to about 150° C. at about 1 atmosphere pressure whereby a composition of matter containing a substantial amount of compound having the structure:

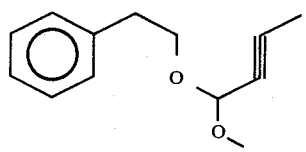

is formed, the reaction being carried out in the presence of an alkali metal hydride.

4. A product produced according to a process comprising the step of intimately admixing the compound having the structure:

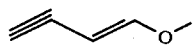

with beta-phenethyl alcohol having the structure:

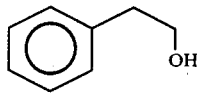

wherein the mole ratio of compound having the structure:

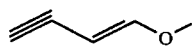

to beta-phenethyl alcohol is about 1:1 at a temperature in the range of from about 100° up to about 150° C. at about 1 atmosphere pressure whereby a composition of matter containing a substantial amount of compound having the structure:

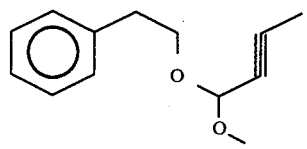

is formed, the reaction being carried out in the presence of an alkali metal hydride, the reaction product being recovered by means of fractional distillation at a temperature in the range of from 128° C. up to 136° C. and at a pressure of from 3.5 mm/Hg pressure up to 3.8 mm/Hg pressure.

5. A product produced according to a process comprising the step of intimately admixing the compound having the structure:

with beta-phenethyl alcohol having the structure:

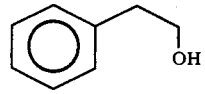

wherein the mole ratio of compound having the structure:

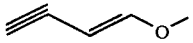

to beta-phenethyl alcohol is about 1:1 at a temperature in the range of from about 100° up to about 150° C. at about 1 atmosphere pressure whereby a composition of matter containing a substantial amount of compound having the structure:

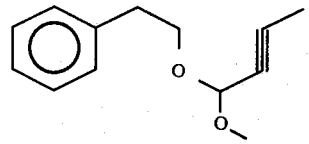

is formed, the reaction being carried out in the presence of an alkali metal hydride, the reaction product being recovered by means of fractional distillation at a temperature in the range of from 84° C. up to 96° C. at 2.2–2.4 mm/Hg pressure.

* * * * *